(12) United States Patent
Le et al.

(10) Patent No.: US 10,098,645 B2
(45) Date of Patent: Oct. 16, 2018

(54) EMBOLIC FRAMING MICROCOILS

(71) Applicant: INCUMEDx, Inc., Fremont, CA (US)

(72) Inventors: Be T. Le, San Jose, CA (US);
Armando Garza, San Jose, CA (US);
Regina C. Velasco, Fremont, CA (US);
Amiel R. Aguilar, San Jose, CA (US);
Berchell J. Yee, Danville, CA (US);
Gregory E. Mirigian, Dublin, CA (US)

(73) Assignee: INCUMEDx, Inc., Fremont, CA (US)

( * ) Notice: Subject to any disclaimer, the term of this patent is extended or adjusted under 35 U.S.C. 154(b) by 242 days.

(21) Appl. No.: 14/634,152

(22) Filed: Feb. 27, 2015

(65) Prior Publication Data
US 2015/0238198 A1 Aug. 27, 2015

Related U.S. Application Data

(60) Provisional application No. 61/945,567, filed on Feb. 27, 2014.

(51) Int. Cl.
*A61M 29/00* (2006.01)
*A61B 17/12* (2006.01)
(Continued)

(52) U.S. Cl.
CPC .. *A61B 17/12145* (2013.01); *A61B 17/00234* (2013.01); *A61B 17/12031* (2013.01);
(Continued)

(58) Field of Classification Search
CPC ........ A61B 17/12113; A61B 17/12031; A61B 17/00234; A61B 2017/00526;
(Continued)

(56) References Cited

U.S. PATENT DOCUMENTS

| 4,994,069 A | 2/1991 | Ritchart et al. |
| 5,108,407 A | 4/1992 | Geremia et al. |

(Continued)

FOREIGN PATENT DOCUMENTS

| AU | 2012202380 A1 | 5/2012 |
| CN | 101045005 A | 10/2007 |

(Continued)

OTHER PUBLICATIONS

International Application No. PCT/US2015/018074, International Search Report and Written Opinion dated Jul. 7, 2015, 16 pages.
Communication Pursuant to Article 94(3) EPC issued for European Patent Application No. 15710996.8-1501 dated Aug. 31, 2017.

*Primary Examiner* — Son Dang
(74) *Attorney, Agent, or Firm* — Goodwin Procter LLP

(57) ABSTRACT

An embolic microcoil can be formed into a complex shape for use in treating aneurysms and other vascular disorders. The microcoil features a distal portion including several loops that together comprise a substantially spherical shape, and an elongated proximal portion that is deployable within the distal portion. The distal portion can create a stable frame with adequate loop coverage across a neck of the aneurysm. The proximal portion can include a series of substantially omega-shaped loops, which can apply a force against the interior of the substantially spherical shaped distal portion, expanding it into apposition with additional portions of the aneurysm wall. Methods of treating vascular disorders and methods of manufacturing certain microcoils are also disclosed.

12 Claims, 11 Drawing Sheets

(51) Int. Cl.
  *A61B 17/00* (2006.01)
  *B21F 3/00* (2006.01)
  *B21F 45/00* (2006.01)

(52) U.S. Cl.
  CPC .......... *A61B 17/12113* (2013.01); *B21F 3/00* (2013.01); *B21F 45/008* (2013.01); *A61B 2017/00292* (2013.01); *A61B 2017/00526* (2013.01); *Y10T 29/49826* (2015.01)

(58) Field of Classification Search
  CPC ......... A61B 2017/00292; B21F 45/008; B21F 3/00; Y10T 29/49826
  See application file for complete search history.

(56) References Cited

U.S. PATENT DOCUMENTS

| | | | |
|---|---|---|---|
| 5,250,071 A | 10/1993 | Palermo | |
| 5,261,916 A | 11/1993 | Engelson | |
| 5,304,194 A * | 4/1994 | Chee | A61B 17/12022 604/104 |
| 5,304,195 A | 4/1994 | Twyford, Jr. et al. | |
| 5,334,210 A | 8/1994 | Gianturco | |
| 5,549,624 A | 8/1996 | Mirigian et al. | |
| 5,562,698 A | 10/1996 | Parker | |
| 5,582,619 A | 12/1996 | Ken | |
| 5,624,449 A | 4/1997 | Pham et al. | |
| 5,624,461 A | 4/1997 | Mariant | |
| 5,639,277 A * | 6/1997 | Mariant | A61B 17/12022 606/191 |
| 5,645,558 A | 7/1997 | Horton | |
| 5,649,949 A * | 7/1997 | Wallace | A61B 17/12022 600/200 |
| 5,658,308 A | 8/1997 | Snyder | |
| 5,700,258 A | 12/1997 | Mirigian et al. | |
| 5,733,329 A * | 3/1998 | Wallace | A61B 17/12022 606/158 |
| 5,749,891 A * | 5/1998 | Ken | A61B 17/12022 606/200 |
| 5,749,894 A | 5/1998 | Engelson | |
| 5,766,219 A | 6/1998 | Horton | |
| 5,891,058 A | 4/1999 | Taki et al. | |
| 5,911,731 A * | 6/1999 | Pham | A61B 17/12022 140/92.1 |
| 5,916,235 A * | 6/1999 | Guglielmi | A61B 17/12022 606/194 |
| 5,935,148 A * | 8/1999 | Villar | A61B 17/12022 606/213 |
| 5,957,948 A | 9/1999 | Mariant | |
| 6,033,423 A | 3/2000 | Ken et al. | |
| 6,036,720 A * | 3/2000 | Abrams | A61B 17/12022 606/200 |
| 6,090,125 A | 7/2000 | Horton | |
| 6,136,015 A | 10/2000 | Kurz et al. | |
| 6,159,165 A | 12/2000 | Ferrera et al. | |
| 6,165,194 A * | 12/2000 | Denardo | A61B 17/12118 606/191 |
| 6,171,326 B1 * | 1/2001 | Ferrera | A61B 17/12022 606/191 |
| 6,231,586 B1 | 5/2001 | Mariant | |
| 6,306,153 B1 | 10/2001 | Kurz et al. | |
| 6,315,709 B1 | 11/2001 | Garibaldi et al. | |
| 6,322,576 B1 | 11/2001 | Wallace et al. | |
| 6,383,204 B1 | 5/2002 | Ferrera et al. | |
| 6,416,541 B2 | 7/2002 | Denardo | |
| 6,605,101 B1 | 8/2003 | Schaefer et al. | |
| 6,616,617 B1 | 9/2003 | Ferrera et al. | |
| 6,635,069 B1 * | 10/2003 | Teoh | A61B 17/12022 606/191 |
| 6,638,291 B1 * | 10/2003 | Ferrera | A61B 17/12022 606/191 |
| 6,656,218 B1 | 12/2003 | Denardo et al. | |
| 6,790,218 B2 | 9/2004 | Jayaraman | |
| 6,802,851 B2 * | 10/2004 | Jones | A61B 17/12022 606/200 |
| 6,855,155 B2 | 2/2005 | Denardo et al. | |
| 6,860,893 B2 | 3/2005 | Wallace et al. | |
| 6,878,163 B2 | 4/2005 | Denardo et al. | |
| 6,913,618 B2 | 7/2005 | Denardo et al. | |
| 6,929,654 B2 | 8/2005 | Teoh et al. | |
| 7,029,486 B2 | 4/2006 | Schaefer et al. | |
| 7,033,374 B2 | 4/2006 | Schaefer et al. | |
| 7,070,608 B2 | 7/2006 | Kurz et al. | |
| 7,316,701 B2 | 1/2008 | Ferrera et al. | |
| 7,326,225 B2 | 2/2008 | Ferrera et al. | |
| 7,331,974 B2 | 2/2008 | Schaefer et al. | |
| 7,422,569 B2 | 9/2008 | Wilson et al. | |
| 7,485,123 B2 | 2/2009 | Porter | |
| 7,842,054 B2 | 11/2010 | Greene, Jr. et al. | |
| 7,879,064 B2 * | 2/2011 | Monstadt | A61B 17/12022 606/200 |
| 8,029,464 B2 | 10/2011 | Wilson et al. | |
| 8,043,321 B2 | 10/2011 | Elliott | |
| 8,066,036 B2 | 11/2011 | Monetti et al. | |
| 8,101,197 B2 | 1/2012 | Buiser et al. | |
| 8,308,751 B2 | 11/2012 | Gerberding | |
| 8,323,306 B2 | 12/2012 | Schaefer et al. | |
| 8,366,738 B2 * | 2/2013 | Dehnad | A61B 17/3207 606/200 |
| 8,377,091 B2 | 2/2013 | Cruise et al. | |
| 8,470,013 B2 | 6/2013 | Duggal et al. | |
| 8,535,345 B2 | 9/2013 | Desai et al. | |
| 8,540,671 B2 | 9/2013 | Wilson et al. | |
| 8,556,927 B2 | 10/2013 | Dehnad | |
| 8,562,667 B2 | 10/2013 | Cox | |
| 8,608,772 B2 | 12/2013 | Wilson et al. | |
| 9,089,405 B1 * | 7/2015 | Gulachenski | A61B 17/12113 |
| 2002/0019647 A1 * | 2/2002 | Wallace | A61B 17/12022 606/200 |
| 2002/0169497 A1 | 11/2002 | Wholey et al. | |
| 2002/0173839 A1 * | 11/2002 | Leopold | A61B 17/12118 623/1.15 |
| 2003/0083735 A1 * | 5/2003 | Denardo | A61B 17/12118 623/1.15 |
| 2003/0216772 A1 | 11/2003 | Konya et al. | |
| 2004/0006354 A1 | 1/2004 | Schaefer et al. | |
| 2004/0098027 A1 * | 5/2004 | Teoh | A61B 17/12022 606/200 |
| 2004/0193206 A1 * | 9/2004 | Gerberding | A61B 17/12022 606/200 |
| 2005/0004598 A1 * | 1/2005 | White, Jr. | A61B 17/12022 606/200 |
| 2005/0107823 A1 * | 5/2005 | Leone | A61B 17/12022 606/200 |
| 2006/0047299 A1 * | 3/2006 | Ferguson | A61B 17/12022 606/200 |
| 2006/0100661 A1 | 5/2006 | Jaeger et al. | |
| 2006/0116712 A1 | 6/2006 | Sepetka et al. | |
| 2006/0241686 A1 * | 10/2006 | Ferrera | A61B 17/12022 606/200 |
| 2007/0088387 A1 * | 4/2007 | Eskridge | A61B 17/12022 606/213 |
| 2007/0142893 A1 | 6/2007 | Buiser et al. | |
| 2007/0175536 A1 * | 8/2007 | Monetti | A61B 17/12022 140/102.5 |
| 2008/0051803 A1 * | 2/2008 | Monjtadt | A61B 17/12022 606/108 |
| 2008/0306503 A1 | 12/2008 | Que et al. | |
| 2010/0023105 A1 * | 1/2010 | Levy | A61B 17/12022 623/1.2 |
| 2011/0245861 A1 * | 10/2011 | Chen | A61B 17/12022 606/200 |
| 2012/0071911 A1 | 3/2012 | Sadasivan et al. | |
| 2012/0209309 A1 | 8/2012 | Chen et al. | |
| 2012/0239074 A1 * | 9/2012 | Aboytes | A61B 17/12113 606/191 |
| 2012/0303052 A1 * | 11/2012 | Connor | A61B 17/12113 606/194 |
| 2012/0303053 A1 | 11/2012 | Chen et al. | |

(56) References Cited

U.S. PATENT DOCUMENTS

| | | | |
|---|---|---|---|
| 2012/0310271 A1* | 12/2012 | Kwon | A61B 17/12022 606/200 |
| 2013/0046326 A1* | 2/2013 | Jones | A61B 17/12113 606/195 |
| 2013/0066357 A1* | 3/2013 | Aboytes | A61M 29/02 606/198 |
| 2013/0066359 A1 | 3/2013 | Murphy et al. | |
| 2013/0116722 A1* | 5/2013 | Aboytes | A61M 29/00 606/198 |
| 2013/0338702 A1 | 12/2013 | Desai et al. | |
| 2014/0081374 A1 | 3/2014 | Kim et al. | |
| 2014/0228939 A1* | 8/2014 | Horton | A61F 2/88 623/1.18 |
| 2015/0289881 A1* | 10/2015 | Suzuki | A61B 17/12031 72/371 |
| 2016/0022445 A1* | 1/2016 | Ruvalcaba | A61B 17/12113 606/198 |
| 2017/0164951 A1* | 6/2017 | Divino | A61B 17/12145 |

FOREIGN PATENT DOCUMENTS

| | | |
|---|---|---|
| EP | 0765636 A2 | 4/1997 |
| EP | 0778006 A1 | 6/1997 |
| EP | 2668914 A1 | 12/2013 |
| EP | 2668915 A1 | 12/2013 |
| JP | 2006239428 A | 9/2006 |
| JP | 2008173497 A | 7/2008 |
| JP | 2010012282 A | 1/2010 |
| WO | WO-1994/011051 A1 | 5/1994 |
| WO | WO-1999/009893 A1 | 3/1999 |
| WO | WO-1999/040852 A1 | 8/1999 |
| WO | WO-2002/045597 A2 | 6/2002 |
| WO | WO-20080151204 A1 | 12/2008 |
| WO | WO-2009/067629 A2 | 5/2009 |
| WO | WO-2010085344 A1 | 7/2010 |
| WO | WO-2012/161509 A1 | 11/2012 |
| WO | WO-2003/039376 A1 | 5/2013 |

* cited by examiner

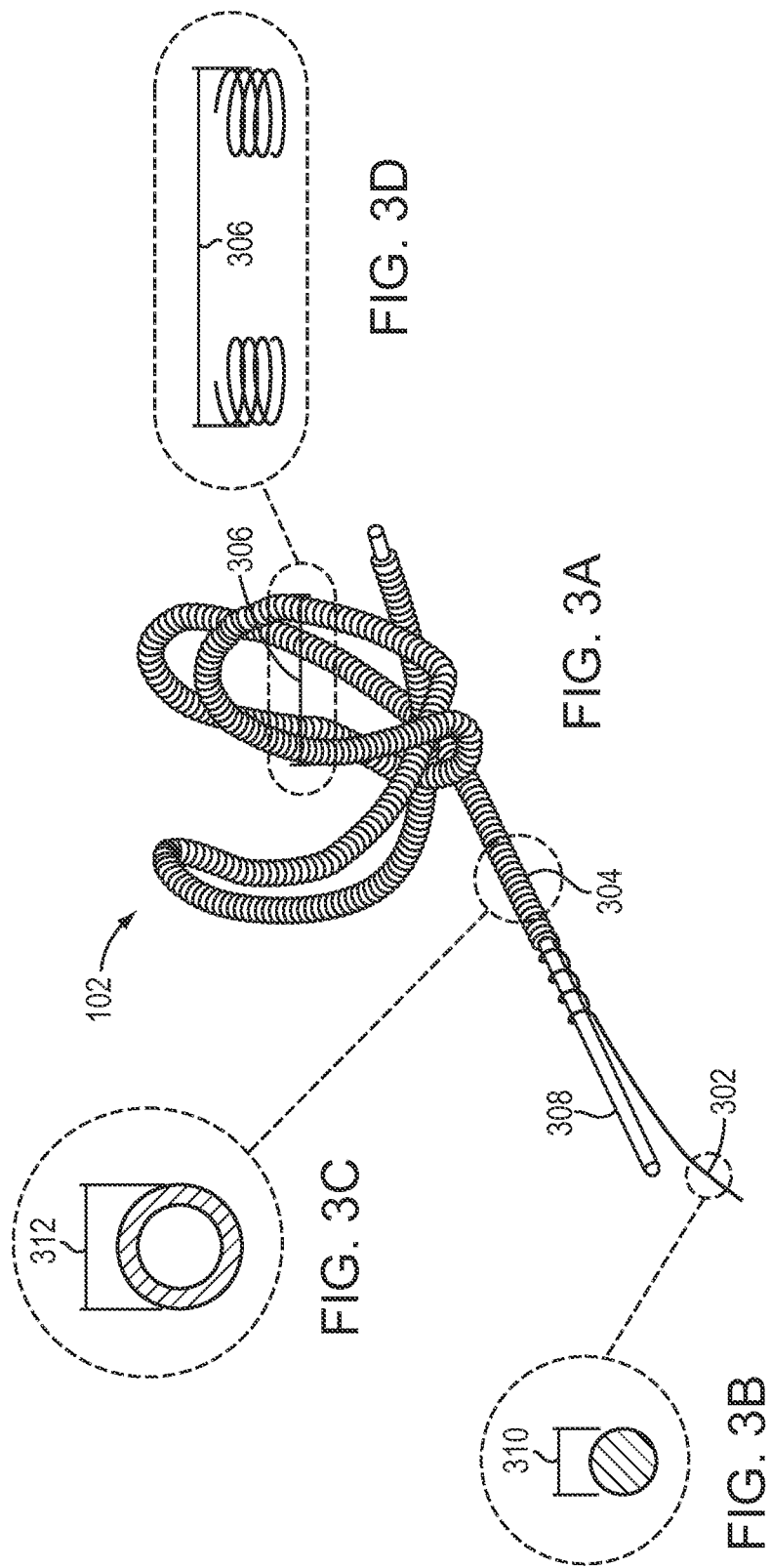

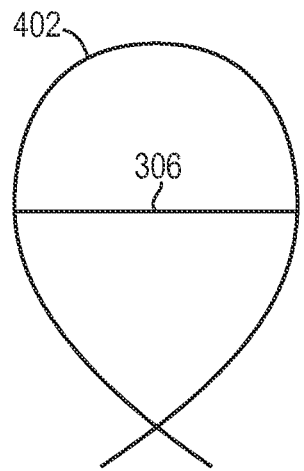
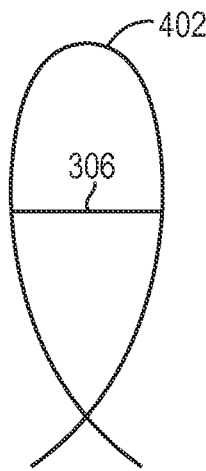
FIG. 4B    FIG. 4C
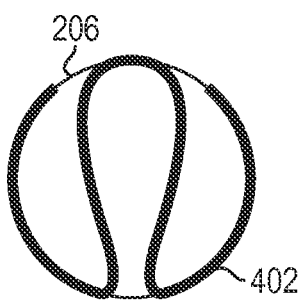
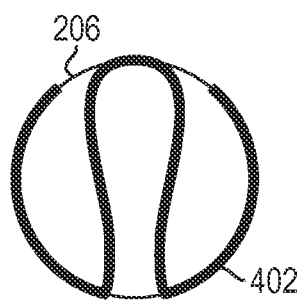
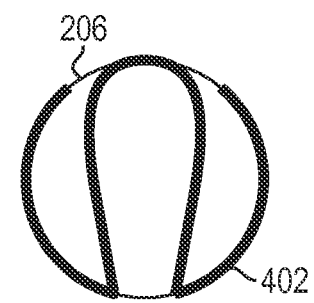
FIG. 5A    FIG. 5B    FIG. 5C
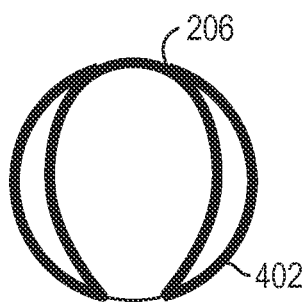
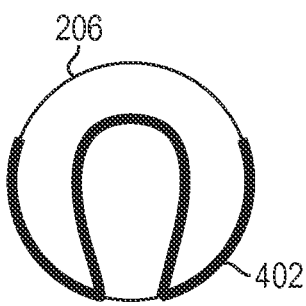
FIG. 5D    FIG. 5E

EMBOLIC FRAMING MICROCOILS

CROSS-REFERENCE TO RELATED APPLICATION

This application claims priority to and the benefit of, and incorporates herein by reference in its entirety, U.S. Provisional Patent Application No. 61/945,567, which was filed on Feb. 27, 2014.

TECHNICAL FIELD

In general, various embodiments of this invention relate to embolic devices for use in the minimally invasive treatment of aneurysms and other vascular disorders and, more particularly, to embolic framing microcoils having various novel shapes that can be used in such treatment.

BACKGROUND

The treatment of aneurysms and other similar vascular disorders often involves the placement of microcoils within a space formed by the aneurysm. This space is often spherical, but in some instances can be elliptical or can have two or more lobular protrusions (often called bi-lobed or multi-lobed aneurysms). Most current microcoil systems have a variety of shapes and can include framing, filling and finishing coils. A framing coil is the first coil placed within an aneurysm and has a complex or three-dimensional shape designed to fit within the space formed by the aneurysm. The framing coil can be used to perform the following functions: (1) provide a stable frame within the confines of the aneurysm into which subsequent coils can be placed; (2) provide adequate loop coverage across a neck of the aneurysm; and (3) prevent loops from crossing the center of the aneurysm (which can create compartments within the aneurysm that require additional catheter manipulation, prolonging the procedure and increasing the risk of aneurysm rupture). Additionally, in some instances, it is desirable for the framing coil to be delivered with minimal or acceptably low friction within a microcatheter. Many framing coils have spherical shapes that can perform these functions when treating a spherical aneurysm; however, they are often inadequate when the aneurysm is non-spherical (e.g., elliptical or bi-lobed). Other framing coils have complex shapes that fit within non-spherical aneurysms; however, such coils typically consist of loops that are arranged with independent axes and are designed to be constrained by the aneurysm itself. This type of shape results in the framing coil having significant potential energy, meaning, for example, that in its unrestrained state it expands well beyond the dimensions of the aneurysm and therefore transfers force directly to the aneurysm wall when constrained in the space. While this force may not be enough to harm the aneurysm wall, it leaves the framing coil in a state susceptible to movement upon placement of subsequent coils. Often times, such coils will shift and potentially cause a loop to protrude into the parent artery, which requires adjunctive and/or emergency therapy. Additionally, the complex shapes of some framing coils often increase the friction created when they are delivered through a microcatheter.

Accordingly, needs exist for improved embolic framing microcoils.

SUMMARY OF THE INVENTION

In various embodiments, the present invention relates to a complex-shaped embolic framing microcoil that can effectively be deployed in aneurysms of a wide variety of shapes and delivered with lower friction than many existing microcoils. In an embodiment, the framing microcoil includes a distal portion having at least two loop elements that form a substantially spherical shape and an elongated proximal portion deployable within the spherical shape and having a series of omega-shaped loops. Such a configuration may, for example, prevent the proximal portion from protruding into the parent artery and help adapt the substantially spherical distal portion to fit various aneurysm morphologies, while maintaining patency within the center of the aneurysm for subsequent microcoils. Although this application often refers to aneurysms, it should be understood that the systems and methods disclosed herein can be adapted for use with any vascular disorder.

In general, in one aspect, embodiments of the invention feature a framing microcoil for use in treating a vascular disorder. The microcoil may include a substantially spherical distal portion and a proximal portion for deployment within the substantially spherical distal portion. The proximal portion may include a series of substantially omega-shaped loops.

In various embodiments, the substantially omega-shaped loops alternate in orientation. In some instances, the series of substantially omega-shaped loops is arranged in a substantially toroid shape when deployed within the substantially spherical distal portion. The toroid shape may be bounded by an interior of the substantially spherical distal portion. In certain instances, the substantially spherical distal portion and/or the proximal portion includes a wire wound to form a primary coil. In some cases, the wire is helically wound and/or includes a platinum alloy. A cross-section of the wire may have a diameter in a range from 0.001 inches to 0.010 inches. A cross-section of the primary coil may have a diameter in a range from 0.008 inches to 0.038 inches. In some instances, the substantially omega-shaped loops are adapted to fit within the substantially spherical distal portion. The omega-shaped loops may be adapted to bias against an interior of the substantially spherical distal portion.

In general, in another aspect, embodiments of the invention feature a method for treating a vascular disorder of a patient. The method can include the steps of positioning a substantially spherical distal portion of a framing microcoil within the vascular disorder, and deploying a proximal portion of the microcoil within the substantially spherical distal portion. The proximal portion may include a series of substantially omega-shaped loops. In various embodiments, the deploying step includes expanding the substantially spherical distal portion outward into apposition with a wall of the vascular disorder.

In general, in yet another aspect, embodiments of the invention feature another framing microcoil for use in treating a vascular disorder. The microcoil includes a substantially spherical distal portion having at least two curved, lobe-shaped loops crossing at a common point.

In various embodiments, the common point is at a base of the substantially spherical distal portion. The curved, lobe-shaped loops may be adapted to expand outward, upon deployment of the microcoil into a vascular disorder, into apposition with a wall of the vascular disorder. In some instances, the curved, lobe-shaped loops are biased outward by another portion of the microcoil deployed within the substantially spherical distal portion, which may include an elongate proximal portion of the microcoil. Each curved, lobe-shaped loop may have a diameter in a range from 1 mm to 24 mm. The substantially spherical distal portion may include between three and six curved, lobe-shaped loops.

In some instances, the microcoil includes a wire wound to form a primary coil. The wire may be helically wound and/or include a platinum alloy. A cross-section of the wire may have a diameter in a range from 0.001 inches to 0.010 inches. A cross-section of the primary coil may have a diameter in a range from 0.008 inches to 0.038 inches.

In some instances, the substantially spherical distal portion includes at least two nested shells. Each shell may have at least one curved, lobe-shaped loop with the curved, lobe-shaped loops crossing at the common point. In such instances, the nested shells can be offset circumferentially at an angle relative to each other (e.g., 90 degrees or 180 degrees).

In general, in still another aspect, embodiments of the invention feature another method for treating a vascular disorder. The method includes the step of positioning within the vascular disorder a framing microcoil that includes a substantially spherical distal portion having at least two curved, lobe-shaped loops crossing at a common point.

In various embodiments, the method further includes the step of expanding at least one of the curved, lobe-shaped loops outward into apposition with a wall of the vascular disorder. This expanding step can include disposing another portion of the microcoil within the substantially spherical distal portion. The method may further include the steps of accessing the vascular disorder with a microcatheter, and deploying the framing microcoil from the microcatheter into the vascular disorder.

In general, in a further aspect, embodiments of the invention feature a method of manufacturing a framing microcoil for use in treating a vascular disorder. The method can include the steps of wrapping a primary coil about a spherical mold having pegs to form a substantially spherical portion including at least two curved, lobe-shaped loops crossing at a common point, and heating the primary coil while wrapped about the mold to set a shape of the primary coil.

In general, in another aspect, embodiments of the invention feature another method of manufacturing a framing microcoil for use in treating a vascular disorder. The method can include the steps of applying a material to an adhesive backed medium in a predetermined pattern including at least two curved, lobe-shaped loops that cross at a common point, wrapping a substantially spherical object with the material and the medium, heating the wrapped object to set a shape of the material, threading a primary coil onto the material, and heating the primary coil while threaded on the material to set a shape of the primary coil.

In various embodiments, the method can further include the step of using a template as a guide when applying the material to the medium. The method can also include the step of securing the material to the object, which may include using a metal foil. In some instances, the method includes the step of placing the wrapped object into a hollowed-out cavity prior to heating the wrapped object. In certain instances, the method includes the step of securing the primary coil to the object, which may include using a metal foil. In some instances, the method includes the step of placing the primary coil threaded on the material into a hollowed-out cavity prior to heating the primary coil.

In general, in yet another aspect, embodiments of the invention feature another framing microcoil for use in treating a vascular disorder. The microcoil includes a substantially spherical portion that includes a series of loops formed in a pattern having two first loops approximately 90 degrees apart, a first plurality of loops formed at incremental angles in a clockwise direction relative to a first one of the two first loops, and a second plurality of loops formed at incremental angles in a counterclockwise direction relative to the first one of the two first loops.

In various embodiments, the loops cross at at least one common point. In some instances, the at least one common point includes two diametrically opposed apex points. In one embodiment, the loops are adapted to expand outward, upon deployment of the microcoil into a vascular disorder, into apposition with a wall of the vascular disorder. The loops may be biased outward by another portion of the microcoil deployed within the substantially spherical portion, which may include an elongate proximal portion of the microcoil. In some instances, the microcoil includes a wire wound to form a primary coil. In some cases, the wire is helically wound and/or includes a platinum alloy. A cross-section of the wire may have a diameter in a range from 0.001 inches to 0.010 inches. A cross-section of the primary coil may have a diameter in a range from 0.008 inches to 0.038 inches.

In general, in still another aspect, embodiments of the invention feature another method for treating a vascular disorder. The method includes the step of positioning within the vascular disorder a framing microcoil that includes a substantially spherical portion having a series of loops formed in a pattern. The pattern includes two first loops approximately 90 degrees apart, a first plurality of loops formed at incremental angles in a clockwise direction relative to a first one of the two first loops, and a second plurality of loops formed at incremental angles in a counterclockwise direction relative to the first one of the two first loops.

In various embodiments, the method further includes the step of expanding at least one of the loops outward into apposition with a wall of the vascular disorder. The expanding step may include disposing another portion of the microcoil within the substantially spherical portion. In some instances, the method further includes the steps of accessing the vascular disorder with a microcatheter, and deploying the framing microcoil from the microcatheter into the vascular disorder.

In general, in a further aspect, embodiments of the invention feature another method of manufacturing a framing microcoil for use in treating a vascular disorder. The method includes the step of wrapping a primary coil about a spherical mold having pegs to form a substantially spherical portion. The substantially spherical portion includes a series of loops formed in a pattern having two first loops approximately 90 degrees apart, a first plurality of loops formed at incremental angles in a clockwise direction relative to a first one of the two first loops, and a second plurality of loops formed at incremental angles in a counterclockwise direction relative to the first one of the two first loops. The method also includes the step of heating the primary coil while wrapped about the spherical mold to set a shape of the primary coil.

These and other objects, along with advantages and features of the embodiments of the present invention herein disclosed, will become more apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 3A is a schematic perspective view showing a wire wound to form a primary coil according to one embodiment;

FIG. 3B is an enlarged view of a portion of FIG. 3A showing a cross-section diameter of a wire;

FIG. 3C is an enlarged view of a portion of FIG. 3A showing a diameter of a primary coil;

FIG. 3D is an enlarged view of a portion of FIG. 3A showing a secondary diameter of a microcoil;

FIGS. 4B and 4C are schematic side views showing curved, lobe-shaped loops having different shapes according to various embodiments;

FIGS. 5A-5E are schematic side views showing various curved, lobe-shaped loops' coverage of an aneurysm wall according to various embodiments;

DESCRIPTION

Figure 1:
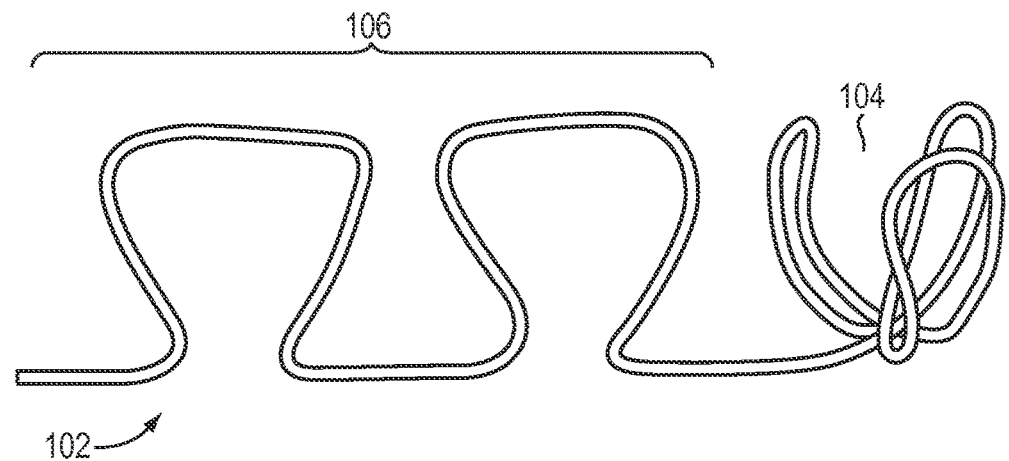
FIG. 1 is a schematic side view of a microcoil that includes an elongated proximal portion and a substantially spherical distal portion according to one embodiment.

Embodiments of the present invention are directed to a complex-shaped embolic framing microcoil, which may include a distal portion and a proximal portion that together form one continuous primary coil. The distal portion may include several individual elements or loops that together form a substantially spherical shape, and the proximal portion may include several elements that form an elongated shape. FIG. 1 shows an exemplary microcoil 102 having a distal portion 104 formed of curved, lobe-shaped loops and a proximal portion 106 formed of omega-shaped loops. However, as will be discussed below, the distal portion 104 and proximal portion 106 may be formed in other shapes as well.

Figure 2:
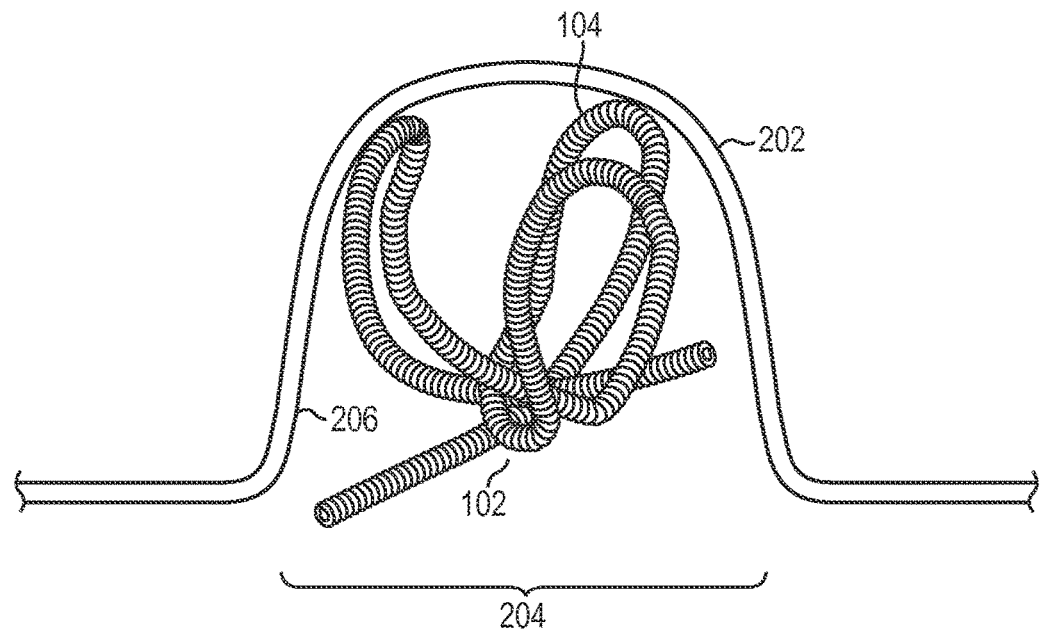
FIG. 2 is a schematic side view of a microcoil placed within an aneurysm according to one embodiment.

With reference to FIG. 2, in one embodiment the microcoil 102 is inserted into an aneurysm 202 (or cavity associated with a similar vascular disorder) such that the distal portion 104 creates a stable frame with adequate loop coverage across a neck 204 of the aneurysm 202. In some instances, the distal portion 104 forms a substantially spherical shape. Following deployment of the distal portion 104, the proximal portion 106 can be deployed within the frame created by the distal portion 104. Both the distal and proximal portions can, in some cases, be deployed by extrusion through a microcatheter. Once deployed, elongated loops of the proximal portion 106 can gently push against an interior of the previously placed substantially spherical distal portion 104, and expand individual loop elements of the distal portion outward. For some aneurysms 202 (e.g., spherically shaped aneurysms), the distal portion 104 may be deployed in apposition with the aneurysm wall 206. In such instances, there may not be room for the distal portion 104 to be significantly expanded by the elongated proximal portion 106, and patency will be maintained in the center of the microcoil mass. For other aneurysms 202 (e.g., irregularly shaped aneurysms), the elongated proximal portion 106 expands certain loops or elements of the distal portion 104 outward to ensure apposition of the coil loops and the aneurysm wall 206.

Referring to FIG. 3A, in some embodiments, the framing microcoil 102 is generally made from wire 302 having a cross-sectional diameter 310 (as shown in FIG. 3B) that is between approximately 0.001" and 0.010", and the wire 302 is wound over a mandrel to create a primary coil 304 with a diameter 312 (as shown in FIG. 3C) between approximately 0.008" and 0.038". For neurovascular aneurysms, the cross-sectional diameter 310 of the wire 302 may be between approximately 0.001" and 0.004", and the wire 302 can be wound to create a primary coil 304 having a cross-ssectional diameter 312 between approximately 0.008" and 0.018". In some instances, the wire 302 is helically wound to form the primary coil 304. In some cases, the wire 302 includes a platinum alloy (e.g., platinum/tungsten). The primary coil 304 can then be wound into various shapes (e.g., loops) having a secondary diameter 306 (as shown in FIG. 3D).

FIG. 3A shows the primary coil 304 wound into three curved, lobe-shaped loops. However, as will be discussed below, in other embodiments the primary coil 304 is wound into other shapes having various secondary diameters. The cross-sectional diameters of the wire 310 and the primary coil 312 can be adjusted to optimize softness (e.g., compliancy and resiliency) for a microcoil having a given secondary diameter 306.

In one embodiment, and with reference still to FIG. 3A, the microcoil also includes a stretch-resistant inner member 308. The inner member 308 can be made from a biocompatible material that adds minimal stiffness but that provides tensile strength, for example a polymer such as monofilament polypropylene.

Figure 4A:
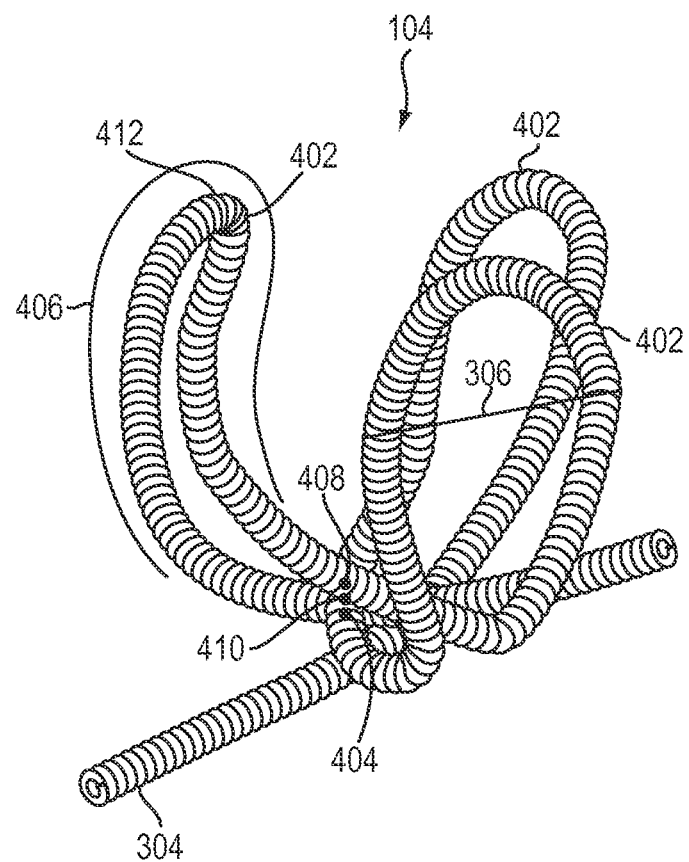
FIG. 4A is a schematic perspective view of a curved, lobe-shaped configuration of the distal portion of a microcoil according to one embodiment.

FIG. 4A shows the substantially spherical distal portion 104 of the microcoil 102 according to one embodiment of the invention. The distal portion 104 includes the primary coil 304 formed into a series of curved, lobe-shaped loops 402. A curved, lobe-shaped loop 402 is a portion of the primary coil 304 shaped such that is has a beginning point 404, a curved section 406 having an apex 412, and an end point 408 that crosses the beginning point 404. The curved, lobe-shaped loops include a secondary diameter 306. The secondary diameter 306 of the curved, lobe-shaped loops can vary in different embodiments of the invention. For example, the curved, lobe-shaped loop 402 shown in FIG. 4B has a larger secondary diameter 306 than the secondary diameter 306 of the curved, lobe shaped-loop 402 shown in FIG. 4C. Generally speaking, if the primary diameter 312 remains constant, as the secondary diameter 306 of a microcoil increases, the friction within a microcatheter upon insertion of the microcoil decreases. This is explained by the fact that friction decreases as stiffness decreases, and the k-factor for stiffness of the microcoil is proportional to the following ratio: primary diameter/secondary diameter. In other words, the stiffness of the microcoil is inversely proportional to the secondary diameter. Thus, the friction within a microcatheter upon insertion of the microcoil is inversely proportional to the secondary diameter 306. Further, applying a similar concept, if the wire diameter 310 remains constant, as the primary diameter 312 increases, the friction within the microcatheter upon insertion of the microcoil generally decreases. This is because the k-factor for stiffness is also proportional to the following ratio: wire diameter/primary diameter. The size of each curved, lobe-shaped loop can be optimized to provide acceptable friction upon insertion into a microcatheter, as well as adequate aneurysm wall coverage.

In some instances, the distal portion 104 includes at least two curved, lobe-shaped loops 402. The number of curved, lobe-shaped loops 402 can vary depending on the secondary diameter 306 and the length of the microcoil used. The beginning and end points of all curved, lobe-shaped loops can cross at a common point 410. In some cases, as shown in FIG. 4A, the common point 410 is located at a base of the distal portion 104. Every other curved, lobe-shaped loop may have a secondary diameter 306 that is equal to or greater than the diameter of the aneurysm intended for embolization. In some instances, each curved, lobe-shaped loop 402 has the same secondary diameter 306. As an example, the secondary diameter 306 can be in a range from 1 mm to 24 mm. In other instances, different curved, lobe-shaped loops 402 have different secondary diameters 306.

In some embodiments, upon deployment of the elongated proximal portion 106 within the distal portion 104, force is exerted by the elongated proximal portion 106 against an interior of the distal portion 104 and each curved, lobe-shaped loop 402 expands outward to fill open space in the aneurysm 202. The number of curved, lobe-shaped loops 402, the height of each curved, lobe-shaped loop 402 (e.g., the distance between the beginning point 404/ending point 408 and the apex 412 of the curved section 406), and the shape of each curved, lobe-shaped loop (e.g., its secondary diameter 306) can all be varied to achieve various amounts of coverage on the aneurysm's interior wall 206, as demonstrated in FIGS. 5A-5E. Depending on the size of the microcoil used, various numbers of curved, lobe-shaped loops 402 may be required to cover the interior wall 206 of a given aneurysm 202. For example, primary coils 304 formed into shapes to fit smaller aneurysms may only require three or four curved, lobe-shaped loops 402, while primary coils 304 formed into shapes to fit larger aneurysms may require four, five or six curved, lobe-shaped loops 402.

Figure 6A:
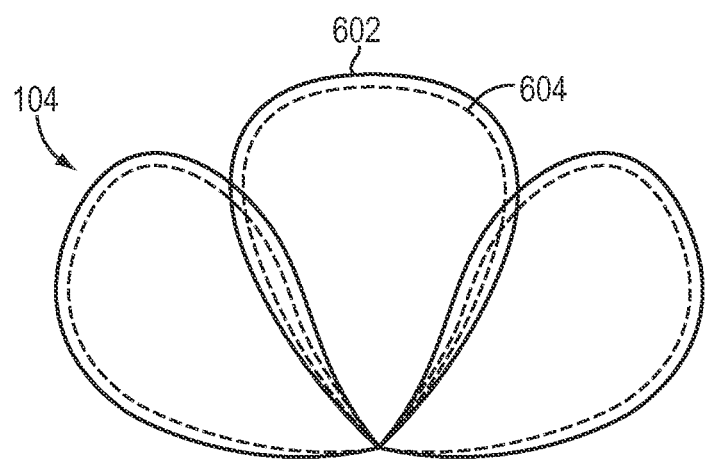
FIG. 6A is a schematic side view of a distal portion of a microcoil having multiple shells of curved, lobe-shaped loops according to one embodiment.
Figure 6B:
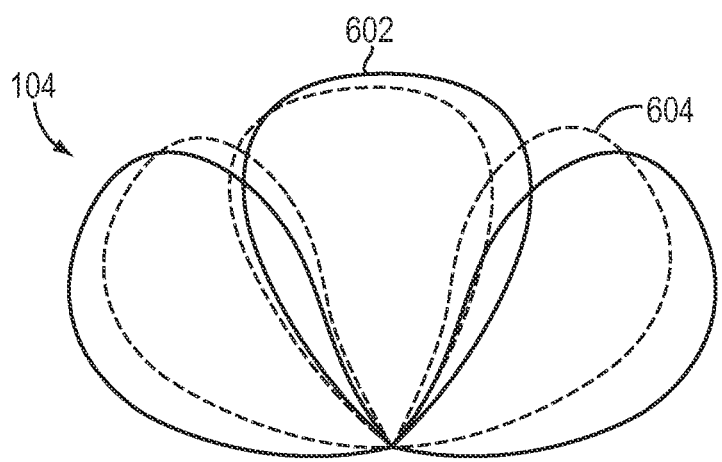
FIG. 6B is a schematic side view of a distal portion of a microcoil having multiple shells of curved, lobe-shaped loops offset circumferentially from one another by an angle according to one embodiment.

In some embodiments, depending on the length of the microcoil used, it may also be desirable to create a shape having overlapping or nested curved, lobe-shaped loops 402. In such embodiments, the curved, lobe-shaped loops 402 can be arranged in two or more shells, with some shells being nested within other shells. For example, as shown in FIG. 6A, a particular distal portion 104 may include multiple curved, lobe-shaped loops 402, with some curved, lobe-shaped loops in an inner shell 602 overlapping (e.g., nested within) other curved, lobe-shaped loops in an outer shell 604. In such embodiments, all the curved, lobe-shaped loops located in every shell can cross at a common point, which in some instances is located at a base of the distal portion 104. In some instances, as shown in FIG. 6B, the shells of curved, lobe-shaped loops may be offset circumferentially from one another such that there is a circumferential angular offset between curved, lobe-shaped loops of different shells. The angular offset can generally be any desired angle, for example 20 degrees, 30 degrees, 45 degrees, 60 degrees, 90 degrees or 180 degrees. At times throughout this application, the configurations of the distal portion 104 described with reference to FIGS. 4A-6B are referred to as "curved, lobe-shaped" configurations.

Figure 7:
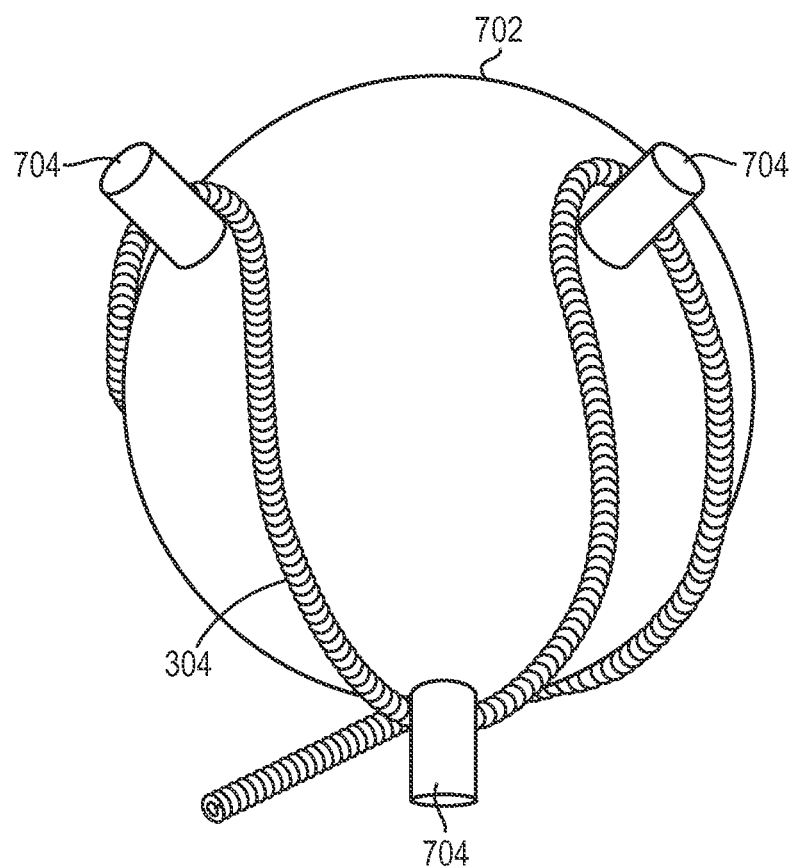
FIG. 7 is a schematic perspective view showing a primary coil wound about a mold to form a curved, lobe-shaped configuration according to one embodiment.

Another aspect of the invention includes a method for manufacturing a framing microcoil having a curved, lobe-shaped configuration for use in treating a vascular disorder. As shown, for example, in FIG. 7, the method can include obtaining a substantially spherical mold 702 having pegs 704. The method can include wrapping a primary coil 304 about the pegs 704 to form a desired shape (e.g., curved, lobe-shaped loops crossing at a common point). The entire assembly (primary coil 304 wrapped about mold 702) can be placed into a high temperature oven to heat set the primary coil 304 into shape. The heating operation can have a shape-set time in a range from 30-180 minutes and a shape-set temperature in a range from 400° C. to 800° C.

Figure 8A:
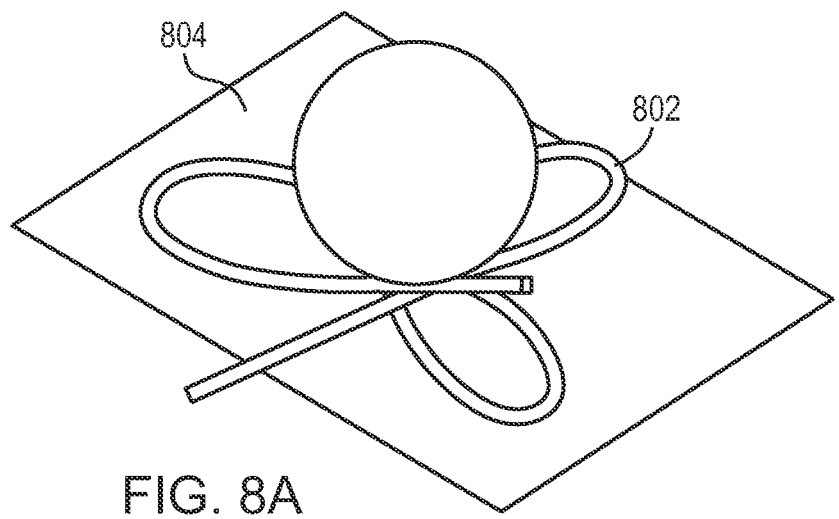
FIGS. 8A-8F are schematic perspective views that illustrate a method of manufacturing the distal portion of a microcoil having a curved, lobe-shaped configuration, according to one embodiment.
Figure 8B:
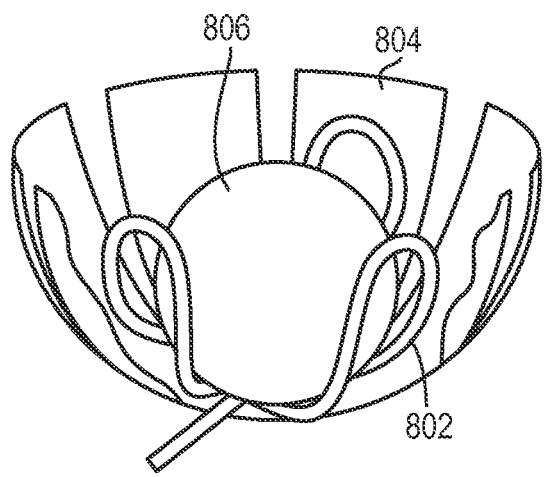
Figure 8C:
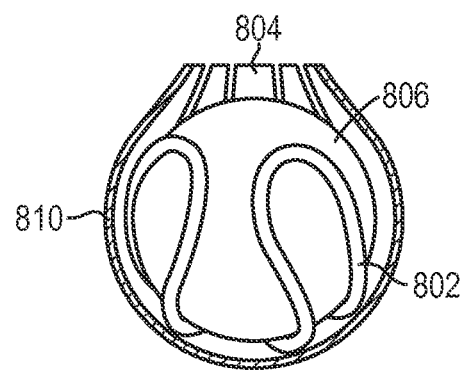

Another aspect of the invention includes another method for manufacturing a framing microcoil having a curved, lobe-shaped configuration for use in treating a vascular disorder. As shown in FIG. 8A, the method can include applying a material 802 (e.g., nitinol wire) to an adhesive backed medium 804 (e.g., an adhesive tape) in a predetermined pattern. In some instances, the pattern includes at least two curved, lobe-shaped loops that all cross at a common point. In some instances, the adhesive backed medium 804 includes a template of the pattern for use as a guide when applying the material 802 to the medium 804. As shown in FIGS. 8B and 8C, the method can include placing a first substantially spherical object 806 in the center of the pattern, and lifting the adhesive backed medium 804 to wrap the material 802 about the first substantially spherical object 806. In certain cases, the first substantially spherical object 806 includes stainless steel. In some embodiments, the material 802 is secured to the first substantially spherical object 806 by wrapping a securing item 810 (e.g., aluminum foil) around the material 802 and the first substantially spherical object 806. In other embodiments, the material 802 is secured to the first substantially spherical object 806 by placing the material 802 and the first substantially spherical object 806 into a hollowed out cavity. The resulting assembly (material 802 adhered to first substantially spherical object 806) can be placed into a high temperature oven to heat set the material 802 into shape. The heating operation can have the same parameters as described above.

Figure 8D:
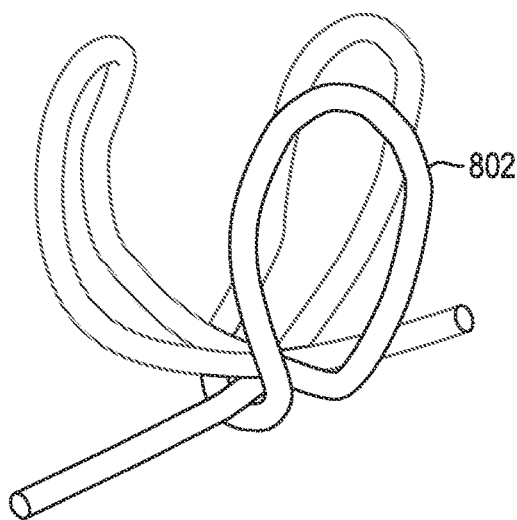
Figure 8E:
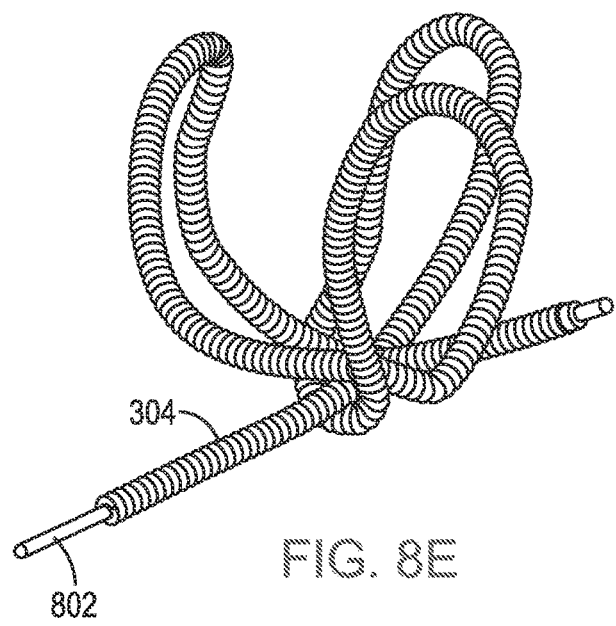
Figure 8F:
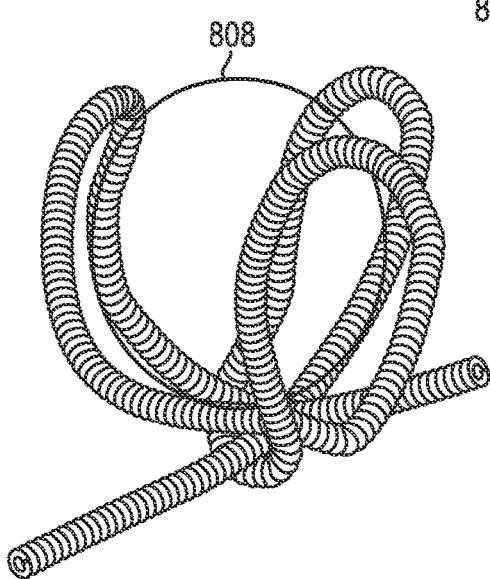

Once heat set into shape, the material 802 can be removed from the first substantially spherical object 806, as shown in FIG. 8D. The method can then include threading a primary coil 304 onto the heat set material 802, as shown in FIG. 8E. The primary coil 304 threaded onto heat set material 802 can then be wrapped about a second substantially spherical object 808, as shown for example in FIG. 8F, and secured thereto using the same techniques for wrapping and securing the material 802 about the first substantially spherical object 806. In some cases, the second substantially spherical object 808 includes stainless steel. In some embodiments, the first substantially spherical object 806 and the second substantially spherical object 808 are the same object. In other embodiments, the first substantially spherical object 806 and the second substantially spherical object 808 are different objects. The resulting assembly (primary coil 304 secured to second substantially spherical object 808) can be placed into a high temperature oven to heat set the primary coil 304 into shape. The heating operation can have the same parameters as described above.

Figure 9:
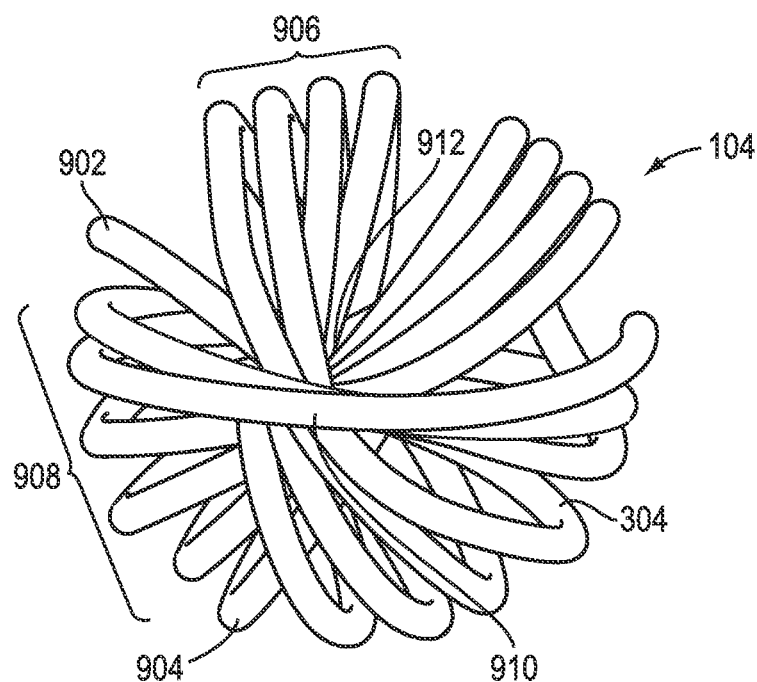
FIG. 9 is a schematic perspective view of a fan-shaped configuration of the distal portion of a microcoil according to one embodiment.

FIG. 9 shows another exemplary configuration of the substantially spherical distal portion 104 according to an embodiment of the invention. The distal portion 104 includes the primary coil 304 wound into a series of loops forming a pattern. The pattern includes two first loops 902, 904 approximately 90 degrees apart. The pattern also includes a first plurality of loops 906 formed at incremental angles in a clockwise direction from one of the first two loops (e.g., loop 902), and a second plurality of loops 908 formed at incremental angles in a counterclockwise direction from one of the first two loops (e.g., loop 902). In some instances, each of the loops in the first plurality of loops 906 are separated from one another by the same incremental angle. Similarly, in some instances, each of the loops in the second plurality of loops 908 are separated from one another by the same incremental angle. In other instances, the loops in the first plurality of loops 906 are separated from one another by different incremental angles. Similarly, in some implementations, the loops in the second plurality of loops 908 are separated from one another by different incremental angles. In some embodiments, the series of loops may cross at at least one common point. In some instances, the at least one common point includes two diametrically opposed apex points 910, 912 of the substantially spherical distal portion 104. At times throughout this application, the configurations of the distal portion 104 described with reference to FIG. 9 are referred to as "fan-shaped" configurations.

Figure 10:
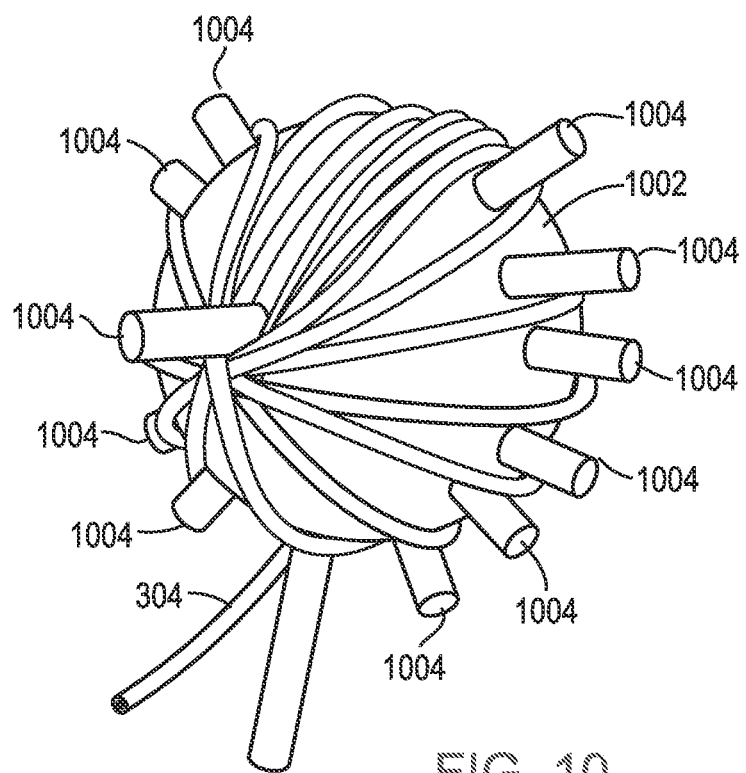
FIG. 10 is a schematic perspective view showing a primary coil wound about a mold to form a fan-shaped configuration according to one embodiment.

Another aspect of the invention includes a method for manufacturing a framing microcoil having a fan-shaped configuration for use in treating a vascular disorder. As shown, for example, in FIG. 10, the method can include obtaining a mold 1002 having pegs 1004. The method can include wrapping a primary coil 304 about the pegs 1004 to form a pattern (e.g., the fan-shaped configuration). The entire assembly (primary coil 304 wrapped about mold 1002) can then be placed into a high temperature oven to heat set the primary coil 304 into shape. The heating operation can have the same parameters as described above.

Figure 11A:
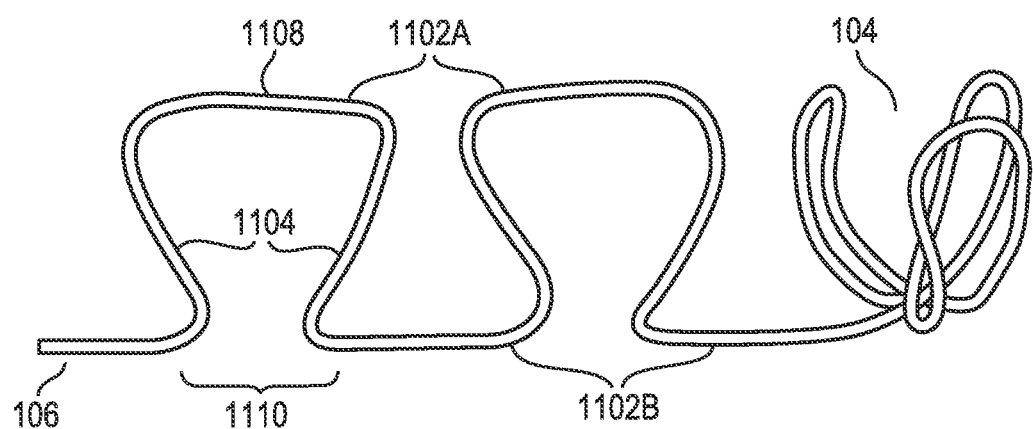
FIG. 11A is a schematic side view showing a proximal portion of a microcoil having omega-shaped loops according to one embodiment.

As discussed above, certain embodiments of the invention feature a microcoil 102 that includes a distal portion 104 (e.g., having a curved, lobe-shaped configuration or a fan-shaped configuration) as well as a proximal portion 106. In some embodiments, the proximal portion 106 includes omega-shaped loops 1102A, 1102B, as shown for example in FIG. 11A. The omega-shaped loops can be formed of a primary coil 304 wound into the loops 1102A, 1102B. With reference to FIG. 11A, an omega-shaped loop includes two legs 1104, a connecting portion 1108 that connects a first end of the two legs 1104, and an incomplete portion 1110 between the second end of the two legs. The legs 1104 can be resilient and/or compliant. In some instances, the omega-shaped loops can alternate in orientation from one another. For example, the omega-shaped loops 1102A alternate in orientation from the omega-shaped loops 1102B. FIG. 11A shows the distal portion 104 as having a curved, lobe-shaped configuration. In general, however, the distal portion 104 connected to the omega-shaped loops can have any configuration, for example the fan-shaped configuration or another substantially spherical configuration. In some embodiments, the proximal portion 106 including the omega-shaped loops 1102A, 1102B is adapted to be deployed within the distal portion 104 to impose a gentle outward force from within the loops of the initially deployed distal portion 104. In some cases, such force can: (1) help stabilize the entire framing infrastructure; (2) significantly enhance the probability of framing irregularly shaped, non-spherical aneurysms (e.g., bi-lobed, ellipsoidal, etc.) by casting or biasing the loops of the distal portion 104 into outer spaces of the aneurysm; (3) increase frame stability within wide-neck aneurysms; and/or (4) maximize the distal portion's contact with the aneurysm wall while minimizing the presence of loops crossing through the central space of the aneurysm.

It can be desirable for the proximal portion 106 to feature omega-shaped loops (or other incomplete loops), because such shapes are better at adapting to various amounts of space within the frame formed by the distal portion 104 than shapes such as complete helical loops. For example, a complete helical loop, if sized too large, may twist or compress toward the center of the space it is filling, which can lead to compartmentalization. If the complete helical loop is sized too small, it may fill the center of the aneurysm, again leading to compartmentalization. Conversely, an omega-shaped loop includes legs 1104 that are resilient and/or compliant such that they can be tuned (e.g., spread further apart or pushed closer together) to adjust the size of the omega-shaped loops. Adjustment of the size of the omega-shaped loops can allow them to fit appropriately within distal portions of varying sizes. In some embodiments, the size of each omega-shaped loop is set during manufacture of the omega-shaped loops (as described below) to fit a distal portion 104 of a particular size. In other embodiments, each omega-shaped loop is manufactured to a standard size, and following disposal of the proximal portion 106 within the distal portion 104, the legs 1104 are adapted to move to improve the fit of the proximal portion 106 within the distal portion 104. In some instances, the spacing between the legs of each omega-shaped loop is substantially the same. In other instances, the spacing between the legs of the omega-shaped loops differ from one another.

Figure 11B:
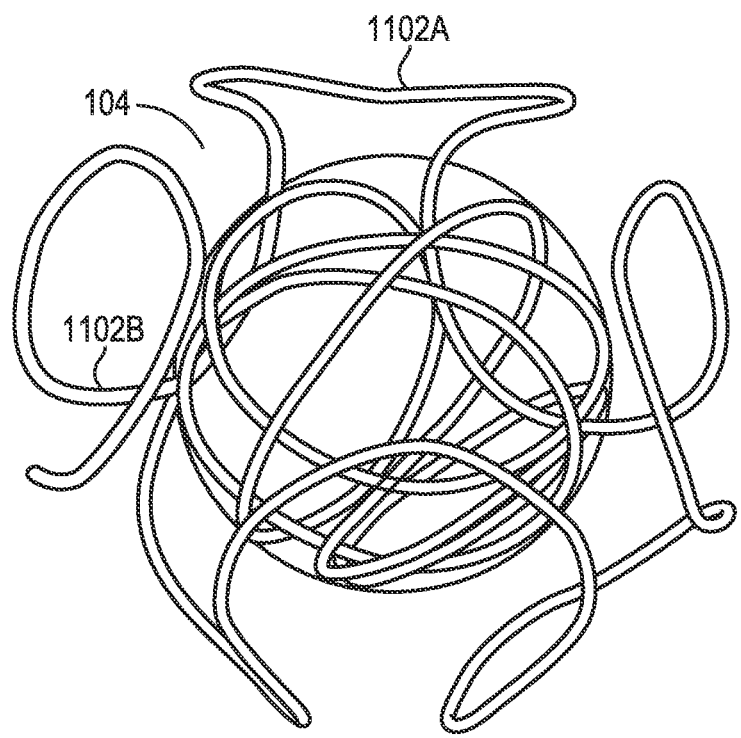
FIG. 11B is a schematic perspective view showing a proximal portion having omega-shaped loops wrapped in a toroid shape about a distal portion of a microcoil, according to one embodiment.
Figure 11C:
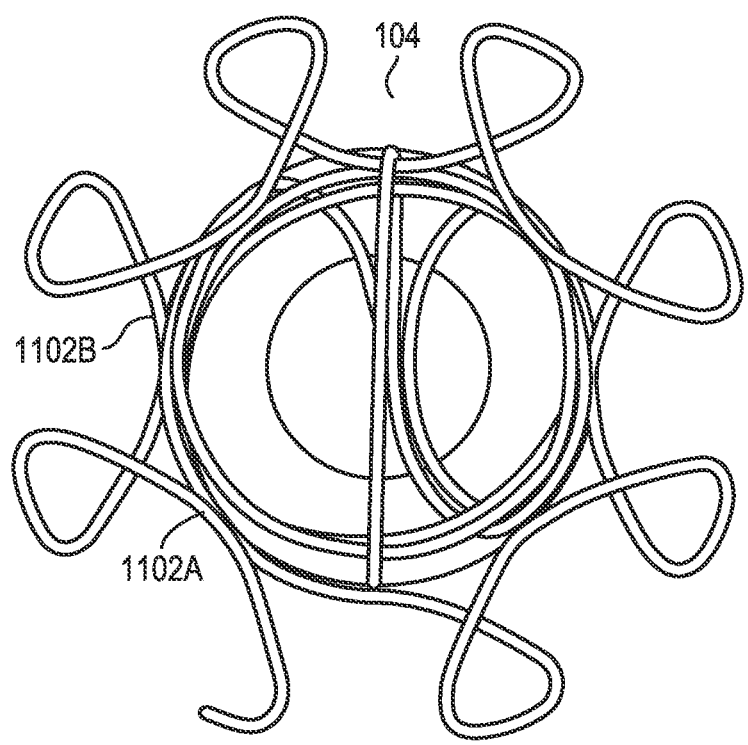
FIG. 11C is a schematic top view showing a proximal portion having omega-shaped loops wrapped in a toroid shape about a distal portion of a microcoil, according to one embodiment.

FIG. 11A is a schematic drawing that illustrates the general shape of the omega-shaped loops; however, FIG. 11A does not depict the orientation of the omega-shaped loops when disposed within the distal portion 104. Examples of such orientations are shown in FIGS. 11B and 11C. As shown, when disposed within the distal portion 104, the omega-shaped loops can be arranged as if they are shaped around a substantially torus or toroid shape, such that they track the shape of the distal portion 104 along the interior of the distal portion 104. In order to clearly depict the omega-shaped loops, FIGS. 11B and 11C depict the omega-shaped loops in a substantially toroid shape along the exterior of the distal portion 104. In reality, however, when deployed, the omega-shaped loops track the interior of the distal portion 104, such that they can apply an outward force to the interior of the distal portion 104.

Another aspect of the invention includes a method for manufacturing the proximal portion 106 including the omega-shaped loops 1102A, 1102B. The method can include obtaining a substantially toroid-shaped object that includes an omega-shaped pattern. This may involve machining an omega-shaped pattern into the substantially toroid-shaped object. The substantially toroid-shaped object can then be combined with a substantially spherical object, which may involve wrapping the substantially toroid-shaped object around the substantially spherical object. A primary coil 304 may then be threaded onto the omega-shaped pattern on the substantially toroid-shaped object. The resulting assembly (primary coil 304 threaded onto the omega-shaped pattern on the substantially toroid-shaped object wrapped around the substantially spherical object) can then be placed into a high temperature oven to heat set the primary coil 304 into shape. The heating operation can have the same parameters as described above.

Other aspects of the invention include methods for treating a vascular disorder that include positioning a microcoil 102 within the vascular disorder. In general, a microcoil 102 may be introduced, delivered, positioned, and implanted within a vascular disorder using a microcatheter. The microcatheter can be a flexible, small diameter catheter having, for example, an inside diameter between 0.016 inches and 0.021 inches. The microcatheter may be introduced by an introducer sheath/guiding catheter combination placed in the femoral artery or groin area of a patient. In some instances, the microcatheter is guided into the vascular disorder with guidewires (e.g., long, torqueable proximal wire sections with more flexible distal wire sections designed to be advanced within tortuous vessels). Such guidewires may be visible using fluoroscopy and may be used to first access the vascular disorder, thereby allowing the microcather to be advanced over it into the disorder.

In some instances, once the tip of the microcatheter has accessed the vascular disorder, the guidewire is removed from the catheter lumen. The microcoil 102 may then be placed into the proximal open end of the microcatheter and advanced through the microcatheter with a delivery mechanism. While the microcoil 102 is disposed within the lumen of the microcatheter it takes the form of a straightened out primary coil. A user (e.g., a physician) may advance and/or retract the microcoil 102 several times to obtain a desirable position of the microcoil 102 within the disorder. Once the microcoil 102 is satisfactorily positioned, it can be released into the disorder. Upon release, the primary coil may form a secondary shape, for example the curved, lobe-shaped configuration, fan-shaped configuration, or any other desired configuration. In some instances, the primary coils' formation of a secondary shape upon deployment into the vascular disorder is caused by the shape-memory nature of the material used to form the microcoil (e.g., nitinol wire). In some instances, the vascular disorder treated is an aneurysm (e.g., a cerebral aneurysm).

In some embodiments, the method for treating a vascular disorder includes positioning, within the vascular disorder, a substantially spherical distal portion 104 of a microcoil 102, and then deploying, within the distal portion 104, a proximal portion 106 of the microcoil 102 having a series of substantially omega-shaped loops. Both the distal portion 104 and proximal portion 106 may be positioned and/or deployed using the techniques described above. In some embodiments, the distal portion 104 includes the curved, lobe-shaped configuration. In other embodiments, the distal portion 104 includes the fan-shaped configuration. In some instances, deploying the proximal portion 106 includes imposing an outward force from within the distal portion 104.

Having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A framing microcoil for use in treating a vascular disorder, the microcoil comprising:
a spheroidal portion, formed from a primary coil itself formed from a helically wound wire, wherein (i) the spheroidal portion comprises at least two curved, lobe-shaped loops crossing at a common point at a base of the spheroidal portion, (ii) apexes of the loops are spaced apart forming an opening at a point on the spheroidal portion diametrically opposite the common point, and (iii) upon deployment of the microcoil into the vascular disorder, the loops are adapted to expand outward into apposition with a wall of the vascular disorder and at least one loop is biased outward by another portion of the microcoil deployed within the spheroidal portion.

2. The framing microcoil of claim 1, wherein the another portion comprises an elongate proximal portion of the microcoil.

3. The framing microcoil of claim 1, wherein each curved, lobe-shaped loop comprises a diameter in a range from 1 mm to 24 mm.

4. The framing microcoil of claim 1, wherein the spheroidal portion comprises between three and six curved, lobe-shaped loops.

5. The framing microcoil of claim 1, wherein the wire comprises a platinum alloy.

6. The framing microcoil of claim 1, wherein a cross-section of the wire comprises a diameter in a range from 0.001 inches to 0.010 inches.

7. The framing microcoil of claim 1, wherein a cross-section of the primary coil comprises a diameter in a range from 0.008 inches to 0.038 inches.

8. The framing microcoil of claim 1, wherein the spheroidal portion comprises at least two nested shells, each shell comprising at least one curved, lobe-shaped loop with the curved, lobe-shaped loops crossing at the common point.

9. The framing microcoil of claim 8, wherein the nested shells are offset circumferentially at an angle relative to each other.

10. The framing microcoil of claim 9, wherein the angle is selected from the group consisting of 90 degrees and 180 degrees.

11. A method for treating a vascular disorder, the method comprising the step of:
positioning within the vascular disorder a framing microcoil comprising a spheroidal portion, formed from a primary coil itself formed from a helically wound wire, wherein (i) the spheroidal portion comprises at least two curved, lobe-shaped loops crossing at a common point at a base of the spheroidal portion and (ii) apexes of the loops are spaced apart forming an opening at a point on the spheroidal portion diametrically opposite the common point; and expanding at least one of the loops outward into apposition with a wall of the vascular disorder, wherein the expanding step comprises disposing another portion of the microcoil within the spheroidal portion.

12. The method of claim 11, further comprising the steps of:

accessing the vascular disorder with a microcatheter; and
deploying the framing microcoil from the microcatheter into the vascular disorder.

\* \* \* \* \*